United States Patent [19]
Nishizawa et al.

[11] Patent Number: 4,477,467
[45] Date of Patent: Oct. 16, 1984

[54] INSECT REPELLENT

[75] Inventors: Kazunori Nishizawa, Sakura; Haruya Kato, Funabashi, both of Japan

[73] Assignee: Kao Soap Co., Ltd., Tokyo, Japan

[21] Appl. No.: 342,404

[22] Filed: Jan. 25, 1982

Related U.S. Application Data

[63] Continuation of Ser. No. 906,590, May 16, 1978, abandoned.

[30] Foreign Application Priority Data

May 19, 1977 [JP] Japan .................................. 52-57934

[51] Int. Cl.³ ..................... A01N 37/00; A01N 37/12; A01N 37/18
[52] U.S. Cl. ........................... 424/317; 424/DIG. 5; 424/DIG. 10; 424/47; 424/69; 424/324
[58] Field of Search ................ 424/324, 317, DIG. 5, 424/DIG. 10

[56] References Cited

FOREIGN PATENT DOCUMENTS 445981 4/1971 Australia ............................ 424/317
493938 1/1977 Australia ............................ 424/317

Primary Examiner—Dale R. Ore
Attorney, Agent, or Firm—Oblon, Fisher, Spivak, McClelland & Maier

[57] ABSTRACT

An insect repellent is disclosed which comprises, as essential ingredients, N,N-diethyltoluamide as a repellent component, and an aromatic proton donor in which the aromatic rings are substituted directly by hydroxyl and/or carboxyl groups. This repellent composition has a longer lasting effect due to increased resistance to absorption through the skin.

3 Claims, 1 Drawing Figure

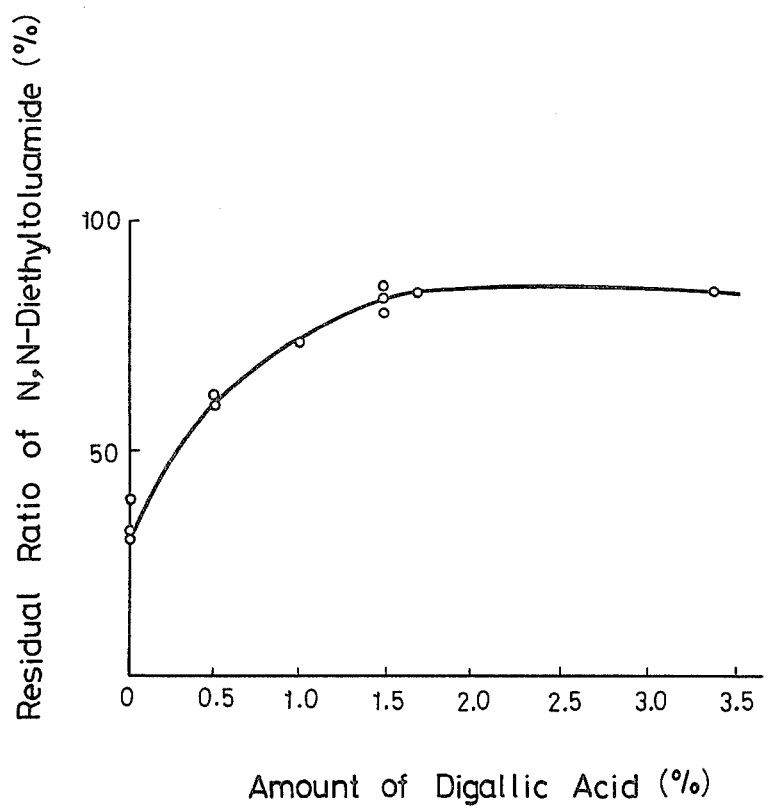

INSECT REPELLENT

This is a continuation of application Ser. No. 906,590, filed May 16, 1978, now abandoned.

BACKGROUND OF THE INVENTION

1. Field of the Invention

This invention relates to insect repellents, and in particular to an insect repellent in which the durability of N,N-diethyltoluamide as a repellent ingredient is increased.

2. Description of the Prior Art

Most mosquitoes among various vectors inhabit warm or torrid zones, but could climatically inhabit a cold district. The mosquitoes attack the exposed skin surface during field work, and often cause infectious diseases and endemic diseases.

In order to repel such insect, many studies on insect repellents have been made and, as a result, a variety of compounds possessing a repellent effect have been found. Among them, N,N-diethyltoluamide is the most suitable for practical use in human beings and finds wide usage at present in view of the durability after application and the strength of effect.

However, N,N-diethyltoluamide has the defect in that the compound is absorbed from the skin into the human body when it is applied to the body surface, and consequently, loses its repellency. N,N-diethyltoluamide becomes more durable when employed in increased amounts, but use of such large amounts gives a sticky feeling to the body and is not practically acceptable. As one attempt to inhibit the absorption from the skin into the body, a method has been reported which comprises forming on the skin a film insoluble in N,N-diethyltoluamide and subsequently coating N,N-diethyltoluamide on the film. In this instance, no satisfactory results are obtainable because the film adheres poorly to the skin.

SUMMARY OF THE INVENTION

In order to surmount the above noted difficulties, the present inventors have made various studies, with their attention directed to the fact that N,N-diethyltoluamide has a carbonyl group which can act as a proton acceptor and that the energy of a hydrogen bond formed with the carbonyl group is far smaller than that a covalent bond. As a result of the studies, they have found that the repellent effect of N,N-diethyltoluamide is not decreased in the least and that the absorption from the skin into the body is significantly inhibited by forming a complex with a proton donor.

Based on this finding, the present invention has been attained.

BRIEF DESCRIPTION OF THE DRAWING

The accompanying drawing shows the relationship between the amount of digallic acid and the residual ratio of N,N-diethyltoluamide.

DETAILED DESCRIPTION OF THE PREFERRED EMBODIMENTS

Suitable proton donors according to this invention are aromatic compounds in which the aromatic rings are substituted directly by hydroxyl and/or carboxyl groups, which proton donors have the formulae (I) and (II),

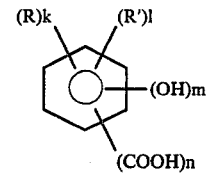

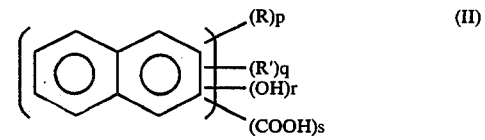

wherein R represents a substituted or unsubstituted alkyl group, a substituted or unsubstituted aromatic ring, a halogen atom, $-NH_2$, $-SO_3H$, $-COOM$, $-OM$ (M is an alkali metal) or $-CHO$. R' represents R''$-COO-$, R''$-O-$, R''$-OOC-$, R''$-OCNH-$, R''NHCO$-$ or R''NH$-$ (R'' is a substituted or unsubstituted alkyl group or a substituted or unsubstituted aromatic ring); k, l, m and n are integers from 0 to 6, respectively, wherein $m+n \geq 1$; and p, q, r and s are integers from 0 to 8, respectively, wherein $R+s \geq 1$.

These proton donors may be further divided as follows:

(1) The compounds in which the monocyclic aromatic compounds are substituted by hydroxy groups [n=0 in the formula (I)]:

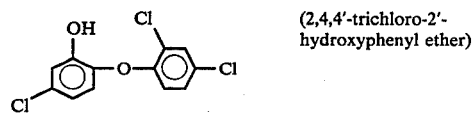
(2,4,4'-trichloro-2'-hydroxyphenyl ether)

(o-phenylphenol)

(hydroquinone)

(hydroxyhydroquinone)

(diresorcinol)

(p-N—ethylaminophenol)

(salicylanilide)

(sodium salicylate)

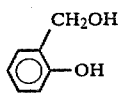 (o-hydroxybenzyl alcohol)

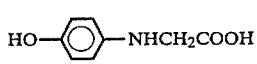 (N—hydroxyphenylglycine)

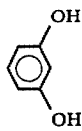 (resorcinol)

(2) The compounds in which the monocyclic aromatic compounds are substituted by carboxyl groups [m=0 in the formula (I)]:

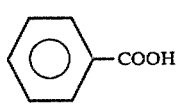 (benzoic acid)

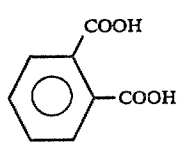 (phthalic acid)

 (terephthalic acid)

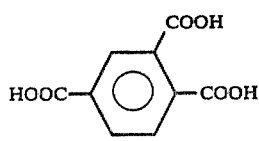 (trimellitic acid)

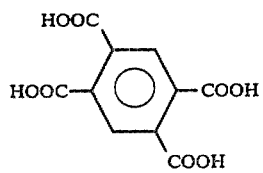 (pyromellitic acid)

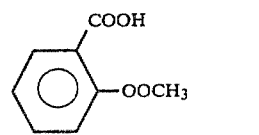 (acetyl salicylic acid)

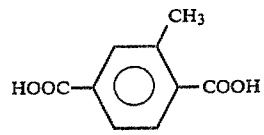 (methylterephthalic acid)

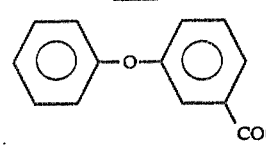 (m-phenoxybenzoic acid)

(3) The compounds in which the monocyclic aromatic compounds are substituted by hydroxyl and carboxyl groups [both m and n are 1 or more in the formula (I)]:

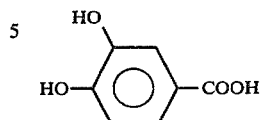 (gallic acid)

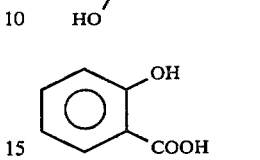 (salicylic acid)

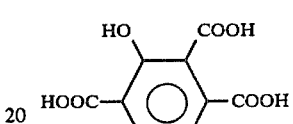 (hydroxytrimesic acid)

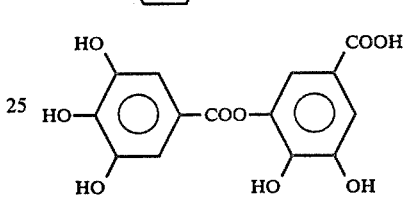 (digallic acid)

tannic acid (4) The compounds in which the polycyclic aromatic compounds are substituted by hydroxyl groups [s=0 in the formula (II)]:

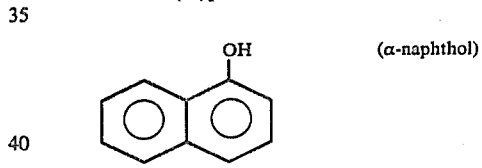

(α-naphthol)

(β-naphthol)

(naphthoresorcinol)

(5) The compounds in which the polycyclic aromatic compounds are substituted by carboxyl groups [r=0 in the formula (II)]:

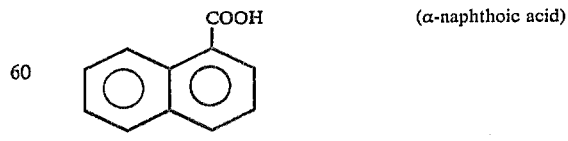 (α-naphthoic acid)

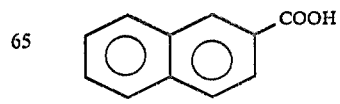 (β-naphthoic acid)

(6) The compounds in which the polycyclic aromatic compounds are substituted by hydroxyl and carboxyl groups [both r and s are 1 or more in the formula (II)]:

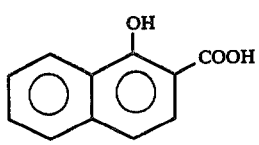

(1-naphthol-2-carboxylic acid)

In order to produce a pest repellent according to the invention, N,N-diethyltoluamide may be mixed with any one of the above proton donors. Preferably, the mixing ratio of both compounds is of such a value that the number of N,N-diethyltoluamide molecules is the same as that of the proton donor groups. In practice, the weight in grams of the proton donor for a given weight of N,N-diethyltoluamide used is 0.5 to 2.0 times the value of Q which is calculated from the following equation:

$$Q = \frac{\text{weight of N,N-diethyltoluamide (g)} \times \text{molecular weight of proton donor}}{191.26 \times \text{number of proton donor groups in one proton donor molecule}}$$

The pest repellent according to the invention can be used in the generally accepted forms such as a solution, lotion, cream, gel, stick, paste, aerosol spray, foam and powder. The content of N,N-diethyltoluamide should be in the range of 1 to 50% by weight, preferably 2 to 30% by weight.

Having generally described the invention, a more complete understanding can be obtained by reference to certain specific examples, which are included for purposes of illustration only and are not intended to be limiting unless otherwise specified.

EXAMPLE 1

Hair was clipped out of the trunks of three hartley strain quinea-pigs, female, weighing 500 to 600 g, to which area the test compositions were applied in an amount of 0.2 mg N,N-diethyltoluamide per/cm². At 3 hours after application, N,N-diethyltoluamide was recovered from the skin surface with acetone and the residual amount was determined by gas chromatography.

| Composition A | |
|---|---|
| N,N—diethyltoluamide | 6 g |
| 2,4,4'trichloro-2'-hydroxyphenyl ether (MW 290) | 9 g |
| ethanol | 35 g |
| water | 50 g |
| Control Composition | |
| N,N—diethyltoluamide | 6 g |
| ethanol | 44 g |
| water | 50 g |

The results obtained are shown in Table 1. The recovery ratio in the Table indicates the weight percent of N,N-diethyltoluamide recovered at 3 hours after application relative to that recovered immediately after application.

TABLE 1

| | Recovery ratio after 3 hours (%) | Average value (%) |
|---|---|---|
| Control Composition | 28.5 28.5 27.6 | 28.2 |
| Composition A | 73.4 80.3 82.1 | 78.6 |

EXAMPLE 2

Using Composition B containing digallic acid as a proton donor, the residual ratio of N,N-diethyltoluamide at 3 hours after application was determined in the same manner as in Example 1. The results obtained are shown in the accompanying drawing.

| Composition B | |
|---|---|
| N,N—diethyltoluamide | 6 g |
| digallic acid | 0–3.36 g |
| water | 50 g |
| ethanol | the rest |
| | 100 g |

EXAMPLE 3

Guinea-pigs, treated with Composition C and the Control Composition of Example 1, in the same manner as in Example 1, were fixed on a holder and placed in a cage in which 30 mosquitoes were released. The number of the mosquitoes that sucked blood within 3 minutes was counted. The results obtained are shown in Table 2.

TABLE 2

| | Number of mosquitoes that sucked blood | | |
|---|---|---|---|
| | After 2 hours | After 4 hours | After 5 hours |
| Untreated | 7 | 7 | — |
| Control Composition | 2* | 7 | 7 |
| Composition C | 1* | 0 | 3* |

*indicates the number of the mosquitoes that sucked blood more than 1 minute after realease in the cage.

| Composition C | |
|---|---|
| N,N—diethyltoluamide | 6 g |
| digallic acid | 1.68 g |
| water | 50 g |
| ethanol | the rest |
| | 100 g |

EXAMPLE 4

The proton donors shown in Table 3 were combined with N,N-diethyltoluamide and the residual ratio of N,N-diethyltoluamide (DET) at 3 hours after application was determined in the same manner as in Example 1. The results obtained are shown in Table 3.

TABLE 3

| Proton donors | | | Composition ratio of proton donor to DET | Residual ratio of DET at 3 hours after application (%) |
|---|---|---|---|---|
| Name of compound | Molecular weight | Number of proton donor groups | | |
| 2,4,4'-trichloro-2'- | 290 | 1 | 1.5 | 81.2 |

TABLE 3-continued

| Name of compound | Proton donors Molecular weight | Number of proton donor groups | Composition ratio of proton donor to DET | Residual ratio of DET at 3 hours after application (%) |
|---|---|---|---|---|
| hydroxyphenyl ether | | | | |
| o-phenylphenol | 170.12 | 1 | 0.89 | 80.3 |
| hydroquinone | 110.11 | 2 | 0.58 | 58.3 |
| benzoic acid | 122.12 | 1 | 0.64 | 76.2 |
| trimellitic acid | 192.13 | 3 | 0.33 | 79.4 |
| gallic acid | 188.14 | 4 | 0.49 | 72.8 |
| tannic acid | 322.22 | 6 | 0.28 | 84.4 |
| α-naphthol | 144.16 | 1 | 0.75 | 73.1 |
| β-naphthic acid | 172.18 | 1 | 0.90 | 61.2 |
| 1-naphthol-2-carboxylic acid | 188.18 | 2 | 0.49 | 76.9 |
| Control | — | — | — | 28.5 |

EXAMPLE 5 (AEROSOL)

| N,N—ethyltoluamide | 6 (w/w %) |
|---|---|
| tannic acid | 1.5 |
| perfume | trace |
| propellant | 50.0 |
| ethyl alcohol | the rest |
| | 100.0 |

EXAMPLE 6 (POWDER)

| N,N—diethyltoluamide | 15.0 (w/w %) |
|---|---|
| tannic acid | 4.2 |
| colloidal silica | 8.5 |
| perfume | trace |
| talc | the rest |
| | 100.0 |

EXAMPLE 7 (LOTION)

| N,N—diethyltoluamide | 20.0 (w/w %) |
|---|---|
| tannic acid | 7.0 |
| perfume | trace |
| isopropyl alcohol | the rest |
| | 100.0 |

EXAMPLE 8 (SPRAY)

| N,N—diethyltoluamide | 3.0 (w/w %) |
|---|---|
| tannic acid | 0.8 |
| di-n-propyl isocinchomeronate | 0.2 |
| N—octylbicycloheptenedicarboxyimide | 1.0 |
| purified petroleum ether | the rest |
| | 100.0 |

What is claimed as new and intended to be secured by Letters Patent is:

1. An insect repellent having increased resistance to absorption through the skin, consisting essentially of 1-50% by weight of N,N-diethyltoluamide as a repellent component, and an aromatic proton donor selected from the group consisting of phthalic acid, terephthalic acid, trimellitic acid, pyromellitic acid, gallic acid, hydroxytrimesic acid, and tannic acid; wherein the weight in grams of said proton donor relative to said N,N-diethyltoluamide is 0.5 to 2.0 times the value of Q which is calculated from the following equation:

$$Q = \frac{\text{amount of N,N—diethyltoluamide (g)} \times \text{molecular weight of proton donor}}{191.26 \times \text{number of proton donor groups in one proton donor molecule.}}$$

2. The insect repellent according to claim 1, wherein said range is from 2 to 30% by weight.

3. A method of increasing the resistance to absorption of N,N-diethyltoluamide through the skin into the body comprising applying an insect repellent complex to the skin, said complex consisting essentially of 1-50% by weight of N,N-diethyltoluamide with an aromatic proton donor selected from the group consisting of phthalic acid, terephthalic acid, trimellitic acid, pyromellitic acid, gallic acid, hydroxytrimesic acid, and tannic acid, wherein the weight in grams of said proton donor relative to said N,N-diethyltoluamide is 0.5 to 2.0 times the value of Q which is calculated from the following equation:

$$Q = \frac{\text{amount of N,N—diethyltoluamide (g)} \times \text{molecular weight of proton donor}}{191.26 \times \text{number of proton donor groups in one proton donor molecule.}}$$

* * * * *